(12) United States Patent
Banerjee et al.

(10) Patent No.: US 9,290,518 B2
(45) Date of Patent: Mar. 22, 2016

(54) WATER SOLUBLE METAL-ORGANIC FRAMEWORKS (MOFS)

(71) Applicant: Council of Scientific and Industrial Research, New Delhi (IN)

(72) Inventors: Rahul Banerjee, Pune (IN); Subhash Chandra Sahoo, Pune (IN); Tanay Kundu, Pune (IN)

(73) Assignee: Council of Scientific and Industrial Research (IN)

( * ) Notice: Subject to any disclaimer, the term of this patent is extended or adjusted under 35 U.S.C. 154(b) by 42 days.

(21) Appl. No.: 14/349,624

(22) PCT Filed: Oct. 3, 2012

(86) PCT No.: PCT/IN2012/000661
§ 371 (c)(1),
(2) Date: Apr. 3, 2014

(87) PCT Pub. No.: WO2013/051035
PCT Pub. Date: Apr. 11, 2013

(65) Prior Publication Data
US 2014/0330020 A1    Nov. 6, 2014

(30) Foreign Application Priority Data
Oct. 3, 2011    (IN) ............................ 2853/DEL/2011

(51) Int. Cl.
C07F 3/06        (2006.01)
C07F 15/00      (2006.01)

(52) U.S. Cl.
CPC ........................................ *C07F 3/06* (2013.01)

(58) Field of Classification Search
USPC ................................... 546/2, 10, 12; 544/226
See application file for complete search history.

(56) References Cited

PUBLICATIONS

"International Application No. PCT/IN2012/000661, International Search Report mailed Apr. 10, 2013", 2 pgs.
Okawa, H., et al., "Oxalate-bridged bimetallic complexes {NH-(prol)3}[MCr(ox)3] (M = Mn(II), Fe(II), Co(II); NH(prol)3(+) = tri(3-hydroxypropyl)ammonium) exhibiting coexistent ferromagnetism and proton conduction", J Am Chem Soc., 131(37), (Sep. 23, 2009), 13516-22.
Sahoo, Subash Chandra, et al., "Helical water chain mediated proton conductivity in homochiral metal-organic frameworks with unprecedented zeolitic unh-topology", J Am Chem Soc., 133(44), (Nov. 9, 2011), 17950-8.

*Primary Examiner* — Charanjit Aulakh
(74) *Attorney, Agent, or Firm* — Schwegman Lundberg & Woessner, P.A.

(57) ABSTRACT

An efficient, one step solution state processing of Proton Conducting Homochiral Metal Organic Framework has been achieved by using derivate of amino acid and Zn(II) salt as a MOF constructor. Control over MOF solubility as well as proton conductivity has also been achieved by judicious selection of the ligand architecture. This invention will lead the way for ease preparation of MOF films for industrial application.

10 Claims, 6 Drawing Sheets

WATER SOLUBLE METAL-ORGANIC FRAMEWORKS (MOFS)

PRIORITY CLAIM TO RELATED APPLICATIONS

This application is a national stage application under 35 U.S.C. §371 of PCT/IN2012/000661, filed Oct. 3, 2012, and published as WO 2013/051035 on Apr. 11, 2013, which claims priority to India Application No. 2853/DEL/2011, filed Oct. 3, 2011, which applications and publication are incorporated by reference as if reproduced herein and made a part hereof in their entirety, and the benefit of priority of each of which is claimed herein.

TECHNICAL FIELD OF THE INVENTION

Present invention discloses biocompatible metal-organic frameworks (MOFs) of formula I that combine a metal and a derivative of an amino acid. Particularly, the invention discloses MOFs of a metal and a derivative of an amino acid which are water soluble.

BACKGROUND AND PRIOR ART OF THE INVENTION

Metal-organic frameworks (MOFs) are a class of new materials well known for their high surface area and pore size. They can be tuned by dictating the various derivatives of amino acids. Most of the reported MOFs in the literature, numbering nearly 25000 till date, are insoluble in water. The brittle nature of these crystalline materials put many challenges for their industrial processing. Further, it is also a challenge to synthesize them in combination with other functional materials without pore blocking and/or decrease of the inner surface area.

Research on Metal-Organic Frameworks (MOFs) has picked up researchers attention because of their diverse topological architectures and applications like gas sorption, catalysis, magnetism and electrical conductivity. Proton (ion) conductivity in solid-state materials are important due to their application in transport dynamics; electrochemical devices, fuel cells and most importantly to understand the complex biological ion channels. For such diverse applications there is a need for the MOFs to have adequate stability in environments that vary in temperature, pressure, water content and such like. A very limited attempt on the proton conductivity on MOFs has been reported where either lattice backbone, added guest molecules like imidazole and 1,2,4-triazole in an anhydrous medium, or water chains and clusters already present inside the framework facilitate proton conduction.

References may be made to Journal J. Am. Chem. Soc. 2009, 131, 13516 by Kitagawa et al. have extensively studied proton conductivity in various MOFs where coordinated water or guest molecules play a vital role in proton conduction. However, the role of halogens (especially halogens coordinated to metals) in controlling proton conduction in MOFs has not been explored at all. Moreover, most of the MOFs, due to their insoluble nature in water can't be fabricated easily as a thin film and usable for proton conduction and various separation applications.

References may be made to Journal entitled "Helical Water Chain Mediated Proton Conductivity in Homochiral Metal_Organic Frameworks with Unprecedented Zeolitic unh-Topology" (JACS) by Sahoo et al which discloses Four new homochiral metal_organic framework (MOF) isomers, [Zn(l-LCl)/(Cl)](H2O)2 (1), [Zn(l-LBr)(Br)]—(H2O)2 (2), [Zn(d-LCl)(Cl)](H2O)2 (3), and [Zn(d-LBr)—(Br)](H2O)2 (4) [L=3-methyl-2-(pyridin-4-ylmethylamino)-butanoic acid], have been synthesized by using a derivative of LID-valine and Zn(CH3COO)2 3 2H2O. A three-periodic lattice with a parallel 1D helical channel was formed along the crystallographic c-axis.

Present invention disclose amino acid based MOFs as a water soluble MOF for industrial application like thin film fabrication etc. which are non-obvious from the point of view that although more than 25000 MOFs have been reported in the literature in the last decade, still most of them are water unstable and thus inappropriate for application in day to day purpose, which narrow down the picture many fold to a few class of MOFs which are water stable. Furthermore, the MOF backbone disintegrates as ligand and corresponding metal oxide/hydroxide by means of which the process become irreversible to reconstruct the MOF. Hence, it will be utmost difficult for a researcher to envisage a homochiral MOF material to be water soluble, which is the most non-obviousness disclosed in the patent. Synthesis of four valine based MOFs in the JACS paper, along with the proton conducting data has been reported. However, the process of water solubility has not been at all discussed anywhere in the paper, which is the most striking feature, as well as the most non-obvious, too. Moreover, in the present patent control over the anion to tune the solubility along with the proton conductivity has achieved. Also, change of the ligand backbone (from valine to alanine) has been achieved to prove the extension of the concept described in the disclosure, which has not been ever discussed in the ma paper. The synthesis of Alanine based MOFs were achieved entirely different procedure described in the JACS paper, as general/straightforward synthetic pathway didn't yield the same. The synthesis of the MOFs with suitable variation of eight synthetic parameters i.e. the ligand backbone, the synthesis temperature, the solvents and their ratio for synthesis, the choice of anion, the reactant ratio and the metal salt as well as the pH of the medium has been reported in the present patent proposal. Hence, under this circumstance we, enable us to claim that any researcher, established and expertise in the synthesis of MOF arena won't be able to synthesize the aforementioned MOFs as now the difficulty level of synthesis has increased eight fold as compared to procedure reported in our JACS paper. Also, the water solubility in non-obvious from the point of view that most of the well known MOFs reported in the literature are water unstable and also they decompose in contact of water. The water solubility information is not reported in JACS paper and also non-obvious for any reader or researcher to envisage the water solubility from the data reported therein. Hence, we have pinpointed the non-obviousness of the process in an elaborated manner along with the new Alanine based MOF structures prepared by suitably adjusting synthesis parameters resulted from the point to point description given in the patent disclosure.

Thus it will highly desirable to have MOFs that have properties that are enlisted herein, but till date, there is no patent or publication available that disclose a MOF with solubility in water. MOFs known in the art, due to their 3-D orientation are known to be water insoluble.

There is therefore a need in the art to provide stable and water soluble MOFs that can be easily fabricated for proton conduction and for various thin film applications.

OBJECTS OF THE INVENTION

The main objective of the present invention is to provide water soluble Metal-Organic Frameworks (MOFs) for synthesizing various functionalized materials for proton conduction as well as for selective separation applications including various thin film applications.

BRIEF DESCRIPTION OF THE DRAWINGS

FIG. 4 represents (a) Photographs of MOF 1 before and after evacuation at 150° C., followed by rehydration showing reappearance of single crystallinity. (b) Appearance and disappearance of water peaks in IR spectra of as-synthesized, evacuated, and rehydrated MOF 1 confirms the reversible transformation. The Solid State Nuclear Magnetic Resonance (SSNMR) spectrum of MOF 1-$D_2O$ ($D_2O$ exchanged sample of MOF1) is shown in the inset. (c) Reversible crystal transformation of MOF 1 confirmed by in situ single-crystal XRD showing the MOF framework with/without solvent (water) as a balland-stick model along the c-axis. Crystallinity of MOF 1 remains intact and suitable for data collection over the temperature, as shown by crystal pictures taken during data collection. (d) Thermal desolvation and in situ VT (variable-temperature) single-crystal experiment of evacuated MOFs 1 and 2 achieved at 80 and 40° C., respectively, confirms that MOF 2 has lower water holding capacity than MOF 1.

FIG. 6 represents 3D representation of the water soluble MOF of the invention. MOF crystallizes in the $P6_1$ space group, which comprises of one Zn(II), one derivative of amino acids and one lattice water molecule in the asymmetric unit. The Zn(II) center adopts a distorted square pyramidal geometry (τ=0.88) chelated by monodentate carboxylate [(Zn1-O2 2.170(3) Å)], and one amino functionality [(Zn1-N1 2.092(4) Å)] of first derivative of amino acids. One pyridyl functionality and one carboxyl oxygen atom of the second derivative of amino acids coordinates in the equatorial positions, and one free chlorine atom occupies the axial site. Noticeably, the amine group is induced by the neighboring chiral carbon center into a homochiral unit to coordinate the zinc atom. As a result, the zinc atom acquires a third homochiral center associated with two homochiral centers. All adjacent zinc nodes are bridged, by pyridyl group to form a $6_1$ helical chain with a pitch of 12 Å along the crystallographic c axis. The two coordinated carboxylate oxygen stay opposite to each other along c axis through which additional molecules derivative of amino acids to form the wall of the helical chain. Among the pyridyl rings along the helical chain, one set of pridyl rings run in clockwise direction while other (linking two molecular chains) run anti clockwise to extend the lattice along the ab-plane. This result in a 3D supramolecular network containing close-packed 1D open channel along the c-axis filled with free water molecules weekly hydrogen bonded to halogen atoms coordinated to metal ions. All pyridyl rings and isopropyl groups constitute the wall of the helical channel and provide a hydrophobic environment to it. This molecular arrangement results in a rare zeolitic unh-topology which has not been perceived so far in any synthetic means even though it is theoretically proposed in ZIFs (Zeolitic Imidazolate Framework).

FIG. 7 represents the schematic process of water solubility exhibited by the water soluble MOF. When a specific amount of water soluble MOF (50 mg) was taken along with specific amount of solvent (2 ml) the MOF shows water solubility, yielding first turbid solution which turns clear upon heating. Both the solution represents the MOF solution in water. To get back or regenerate the original MOF material, only one step is necessary is that to heat the solution at 90° C. to take out the water.

SUMMARY OF THE INVENTION

Accordingly, present invention provides stable, water soluble and biocompatible metal organic frameworks (MOFs) of formula I $$[M(l/d\text{-}L_X)(X)](H_2O)_2 \qquad \text{Formula I}$$

wherein

M is a metal selected from the group consisting of Sc, Ti, V, Cr, Mn, Fe, Co, Ni, Cu, Zn, Y, Zr, Nb, Mo, Tc, Ru, Rh, Pd, Cd, La, W, Os, Ir, Pt, Au, Hg, Sm, Eu, Gd, Tb, Dy, Ho, Al, Ga, In, Ge, Sn, Pb), Li, Na, K, Rb, Cs, Mg, Ca, Sr or Ba;

L is derivatives of an amino acid ligand of formula II

Formula II wherein $R_1$=methyl or isopropyl; $R_2$=pyridyl, bipyridyl, imidazoleyl, piparizineyl, napthayl, tetrazoleyl and nitrogen containing heterocycles;

X=CH3COO or HCOO when R1=isopropyl in Ligand L of formula II;

X=Cl, Br, CH₃COO or HCOO; when R1=methyl in Ligand L of formula II.

In an embodiment of the present invention, representative compounds of said MOF comprising:

[Zn(l-L1$_{CH3COO}$)(CH₃COO)](H₂O)₂ (5); wherein R1=isopropyl, R2=pyridyl in ligand L;

[Zn(l-L1$_{HCOO}$)(HCOO)](H₂O)₂ (6); wherein R1=isopropyl, R2=pyridyl in ligand L;

[Zn(l-L2$_{Cl}$)(Cl)](H₂O)₂ (7); wherein R1=methyl, R2=pyridyl in ligand L;

[Zn(l-L2$_{Br}$)(Br)](H₂O)₂ (8); wherein R1=methyl, R2=pyridyl in ligand L;

[Zn(l-L2$_{CH3COO}$)(CH₃COO)](H₂O)₂ (9); wherein R1=methyl, R2=pyridyl in ligand L;

[Zn(l-L2$_{HCOO}$)(HCOO)](H₂O)₂ (10); wherein R1=methyl, R2=pyridyl in ligand L

In yet another embodiment of the present invention, the derivative of an amino acid ligands of formula II is selected from the group consisting of:

1

2

3

4

5

6

7

8 in yet another embodiment of the present invention, water solubility of compound of formula 1

Formula II wherein $R_1$=methyl or isopropyl; $R_2$=pyridyl, bipyridyl, imidazoleyl, piparizineyl, napthayl, tetrazoleyl and nitrogen containing heterocycles; X=Cl, Br, $CH_3COO$ or HCOO; when R1=methyl or isopropyl in Ligand L of formula II are in the range of 20-28 mg/ml.

In yet another embodiment of the present invention, the biocompatible metal organic frameworks are useful for proton conduction.

In yet another embodiment of the present invention, proton conductivity of the said MOFs is in the range of $3.6 \times 10^{-5}$ S $cm^{-1}$ to $3.5 \times 10$ S $cm^{-1}$.

In an embodiment, present invention also provides a process for preparation of biocompatible water soluble metal organic frameworks (MOF) prepared under hydrothermal conditions and the said process comprising the steps of:
a) adding metal salt to an aqueous solution of derivative of an amino acid in the ratio ranging between 1:1 to 1:2 followed by sonicating to obtain clear solution;
b) keeping the tightly capped solution as obtained in step (a) undisturbed, at temperature in the range of 50 to 90° C. to obtain transparent crystals of water soluble metal organic framework (MOF) of formula I.

In yet another embodiment of the present invention, metal salt is zinc acetate.

DETAILED DESCRIPTION OF INVENTION

Present invention provides stable, water soluble biocompatible Metal organic frameworks (MOFs) of formula I comprises a metal and derivatives of an amino acid ligand L of formula II $[M(l/d-L_X)(X)](H_2O)_2,$   Formula I wherein M is metal;
X is a anion selected from Cl, Br, $CH_3COO$ or HCOO.

L is derivatives of an amino acid ligand of formula II and The metal of the water soluble MOF of the invention is selected from d-block metals ($M^{+n}$=Sc, Ti, V, Cr, Mn, Fe, Co, Ni, Cu, Zn, Y, Zr, Nb, Mo, Tc, Ru, Rh, Pd, Cd, La, W, Os, Ir, Pt, Au, Hg), f-block metals ($M^{+n}$=Sm, Eu, Gd, Tb, Dy, Ho), p-block metals ($M^{+n}$=Al, Ga, In, Ge, Sn, Pb), alkali metals ($M^{+n}$=Na, K, Rb, Cs), alkaline earth metals ($M^{+n}$=Mg, Ca, Sr, Ba) and such like.

The derivative of an amino acid (L) is selected from

Formula II wherein $R_1$ is side chain residue of amino acids;

R1 is methyl for Alanine and isopropyl for valine.
$R_2$=pyridyl, bipyridyl, imidazoleyl, piparizineyl, napthayl, tetrazoleyl and nitrogen containing heterocycles,

Some preferred derivative of an amino acid ligand of the water soluble MOF of the invention are selected from the group consisting of

1

2

3

4

-continued

5

6

7

8

The MOFs of the invention is prepared by a process under hydrothermal conditions comprising:
a) adding metal salt to an aqueous solution of derivative of an amino acid followed by sonicating the solution to obtain clear solution and
b) keeping the tightly capped solution undisturbed at 90° C. to obtain transparent crystals of water soluble MOF.

Accordingly, to an aqueous solution (2 ml) of derivative of an amino acid (0.2 mmol), suitable metal salt (0.1 mmol) was added and sonicated for 10 min. The clear solution was kept in a tightly capped 5 ml vial for 24 h at 90° C. to produce rod shaped transparent crystals of water soluble MOF (Solubility is 20 mg/ml of water). One preferred metal salt according to the invention is Zn salt, preferably Zn acetate.

The MOF is characterized by its 3D coordinates as exemplified herein. The MOF is tested for solubility in water by boiling it in water for few minutes. The MOF dissolves in boiling water and on evaporation of the solvent water, the crystallized MOF has been characterized.

Saturated solutions of the MOF can be made by adding excess MOF into the solution and filtering out the undissolved portion. Such water soluble MOFs are proton conducting and can be fabricated for various thin film applications. The present MOF, due to its easy solubility and stability in water has major advantage over the known MOFs and thus can easily be fabricated for various thin film applications. Due to its solubility in water, a rarely observed phenomenon, as compared to reported' MOFs, it can provide a new pathway for synthesizing various functionalized materials for selective separation applications.

Present invention provides six novel biocompatible homochiral metal organic framework (MOF) isomers have been synthesized by using a derivative of L-/D-valine and $Zn(CH_3COO)_2.2H_2O$ and studied for their proton conductivity.

(5)

(6)

(7)

(8)

(9)

(10).

These MOFs are characterized by single crystal X-ray diffraction (SCXRD), thermogravimetric analysis (TGA), powder X-ray diffraction (PXRD), circular dichroism (CD), and hot-stage microscopy. The mobility of the water molecule with respect to temperature has been monitored by in situ variable-temperature powder X-ray diffraction (VT-PXRD) and single-crystal to single-crystal (SC-SC) transformation experiments. The ordered water molecules anchored by weak metalhalogen groups facilitate proton conduction, as confirmed by proton conductivity measurements coupled with deuterium exchange and solid-state (SS) NMR experiments. MOFs such as [Zn(l-L1Cl)(Cl)](H2O)2 (1) and [Zn(d-L1Cl)(Cl)](H2O)2 (3), due to this helical water chain, exhibit a high proton conductivity of ~4.45×10-5 S cm-1 at ambient temperature, while MOFs [Zn(l-L1Br)(Br)](H2O)2 (2) and [Zn(d-L1Br)(Br)](H2O)2 (4) show almost zero proton conductivity, even though all four MOFs adopt similar architectures [L=3-methyl-2-(pyridin-4-ylmethylamino)butanoic acid].

Figure 1:
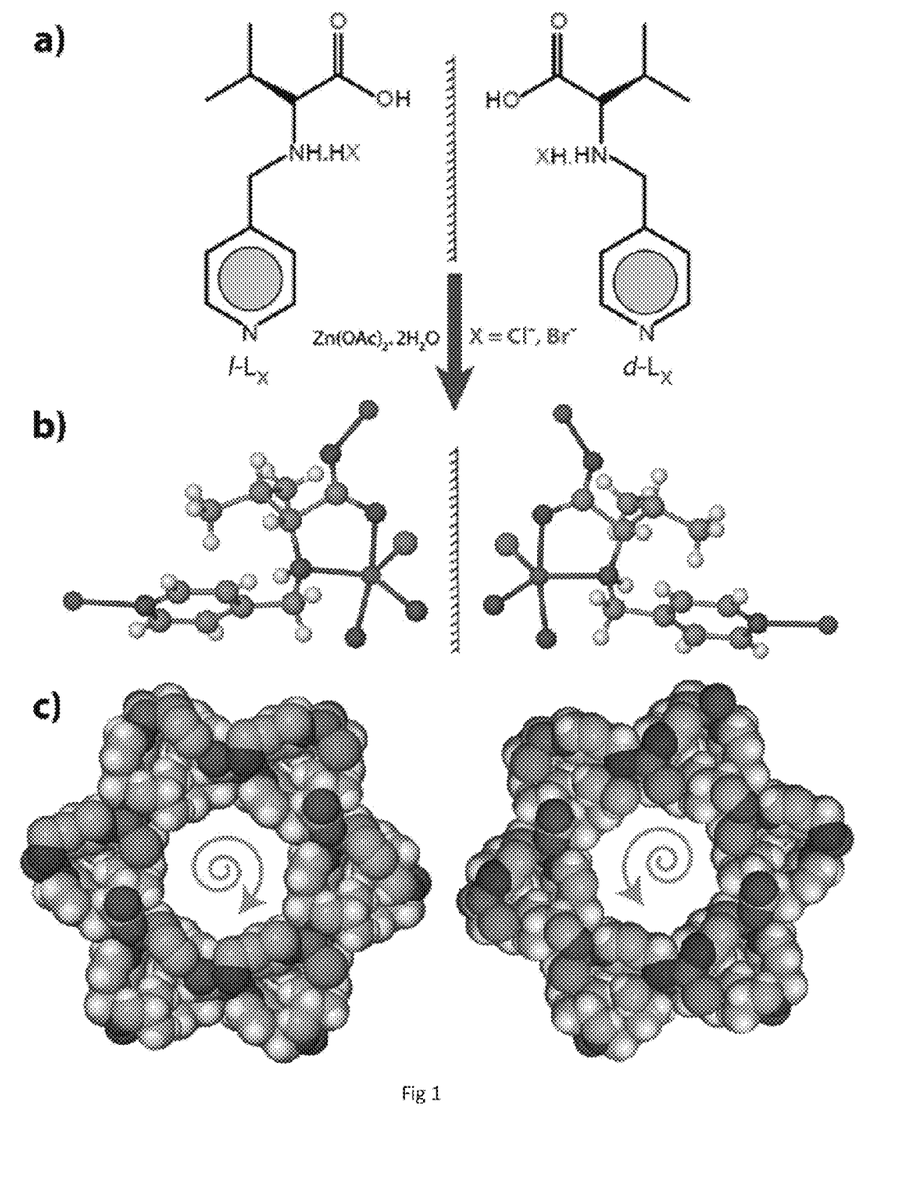
FIG. 1 represents (a) schematic representation of the links with mirror isomers (l-$L_X$) and (d-$L_X$) in the form of different salts, where X=Cl, Br are shown in green. (b) Ball and stick model of an asymmetric unit of MOFs with mirror isomers, showing a five-coordinated zinc center (pink ball): (c) Space-filling model of two enantiomers of MOF 1 and 3. Opposite helicity is shown as a blue curved arrow. Colour code: gray, Cl; green, Cl; red, 0; blue, N; pink, Zn; white, H.

MOFs 1-6 reported here were synthesized by mixing $Zn(CH_3COO)_2.2H_2O$ and 3-methyl-2-(pyridin-4-ylmethylamino) butanoic acid (a valine-derived link) (FIG. 1a) under hydrothermal conditions in water medium. Phase-pure rod shaped crystals were grown in a capped vial at 90° C. within 5-6 h. MOFs 1-6 are structural isomers with different anions (Cl or Br or $CH_3COO$ or HCOO) coordinated to the metal atoms or enantiomers with respect to ligand backbone (d or l). MOF 1 crystallizes in the P61 space group, comprising one Zn(II), one l-$L_{Cl}$ ligand, and two lattice water molecules in the asymmetric unit. The Zn(II) center adopts a distorted square pyramidal geometry (r=0.38), chelated by monodentate carboxylate [(Zn1O2 2.170(3) Å)] and one amino functionality [(Zn1N1 2.092(4) Å)] of the first l-$L_{Cl}$ link. One pyridyl functionality and one carboxyl oxygen atom of the second l-$L_{Cl}$ ligand coordinate in the equatorial positions, and one free chlorine atom occupies the axial site (FIG. 1b). Noticeably, the amine group is induced by the neighboring chiral carbon center into a homochiral unit to coordinate the zinc atom. As a result, the zinc atom acquires a third homochiral center associated with two homochiral centers. All adjacent zinc nodes are bridged by pyridyl groups to form a $6_1$ helical chain with a pitch of 12 Å along the crystallographic c-axis (FIG. 1c). The two coordinated carboxylate oxygens stay opposite to each other along the c-axis, through which additional molecules link to form the wall of the helical chain.

Figure 2:
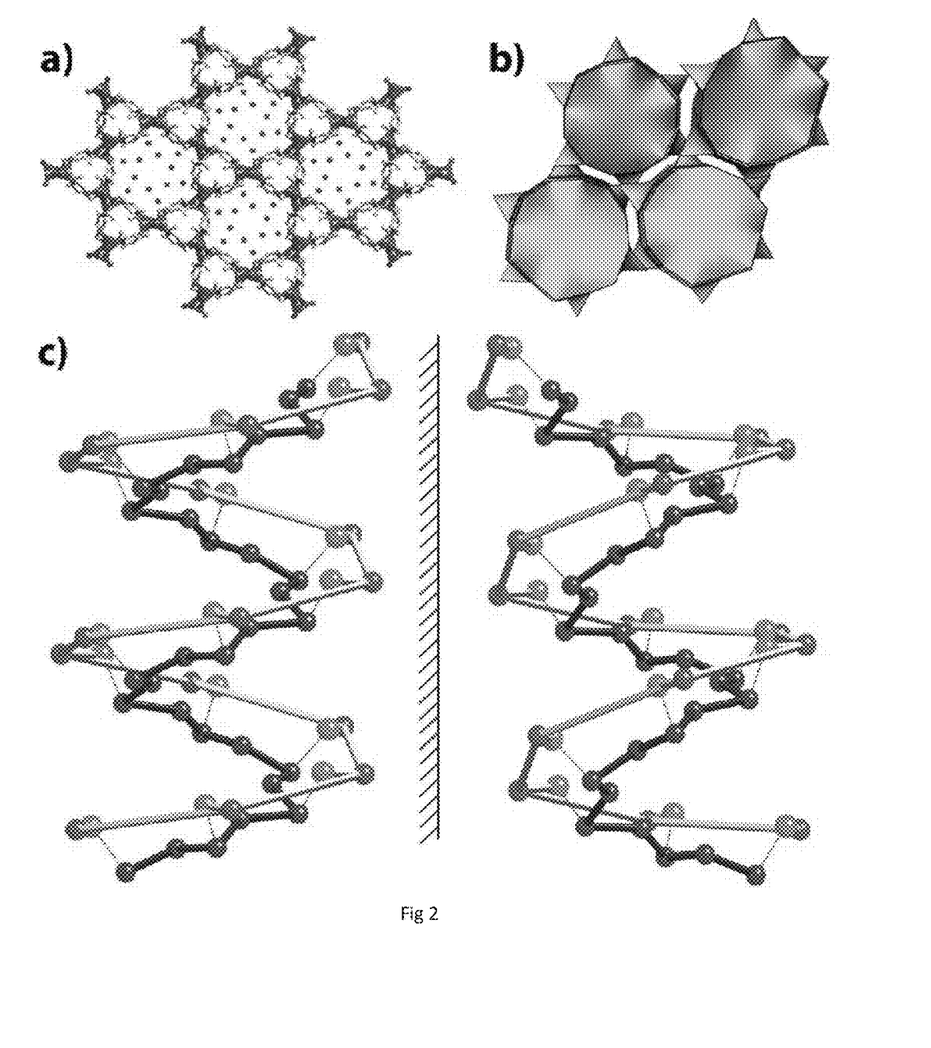
FIG. 2 represents (a) Polyhedral representation of the MOF 1 lattice viewed down the c-axis. Pink polyhedra represent zinc centers, and lattice water molecules are shown as red balls. (b) Tiling figure of MOF 1, showing zeolitic unh-topology (unh is a three letter code representing the topology (structural arrangement) of a zeolite) along the c-axis. The tiling shows one kind of vertices, two kinds of edges, two kinds of faces, and one kind of tiles. (c) Mirror isomers of helical water chains surrounded by a molecular helix (outer helix). The molecular helix (outer helix) is shown as pink balls connected via gray bonds, and the helical water chain (inner helix) is shown as red balls connected via blue rods.

Among the pyridyl rings along the helical chain, one set of pridyl rings run in a clockwise direction while the others (linking two molecular chains) run anti-clockwise to extend the lattice along the ab-plane. This results in a 3D supramolecular network containing a close-packed 1D open channel along the c-axis filled with water molecules (FIG. 2a). Pyridyl rings and isopropyl groups constitute the wall of the helical channel, providing a hydrophobic environment. This molecular arrangement results in a rare zeolitic unh-topology which has not been perceived so far in any synthetic means, even though it is theoretically proposed in ZIFs.

Lattice water molecules weakly H-bonded to the M-Cl atom (O . . . . Cl-M, 3.175(1) Å) run along the helical channel (FIG. 2c). The second water molecule resides within H-bonding distance of the first water molecule (DO . . . O=3.234(3)Å) to make a continuous water channel along the c-axis. This H-bonding distance is well within the range of DO . . . O of O—H . . . O hydrogen-bonding reported in the literature. As a result, a secondary helical water chain surrounded by the molecular helix is formed. Weak (O—H . . . Cl-M) H-bonding may allow the water protons to become more acidic. It was found that the helical orientation of
water molecules is the structural basis by which K+ ion and proton transport occurs inside a KcsA K+ channel and in protein aquaporin-1, respectively. 1D water chains also play vital roles for stabilizing the native conformation of biopolymers, but such helical water chains are less reported in synthetic homochiral crystal hosts, especially in MOFs, because in most cases high boiling solvents like DMF, DMA, DMSO, and DEF are used for MOF synthesis instead of water.

Single-crystal XRD analysis revealed that MOFs 2, 3, 4, 5 and 6 are isomorphous to MOF 1, where ½ and ¾ are isomers with respect to substituted halogen atoms, like 1 [L$_2$M-Cl] and 2 [L$_2$M-Br], but ⅓ and ⅔ are enantiomers. In further experiments, it has been confirmed that all six isomers possess similar lattice arrangement (unh-topology) and the helical water chain persists irrespective of the different anion substitution or change in chirality of the ligand backbone.

Figure 3:
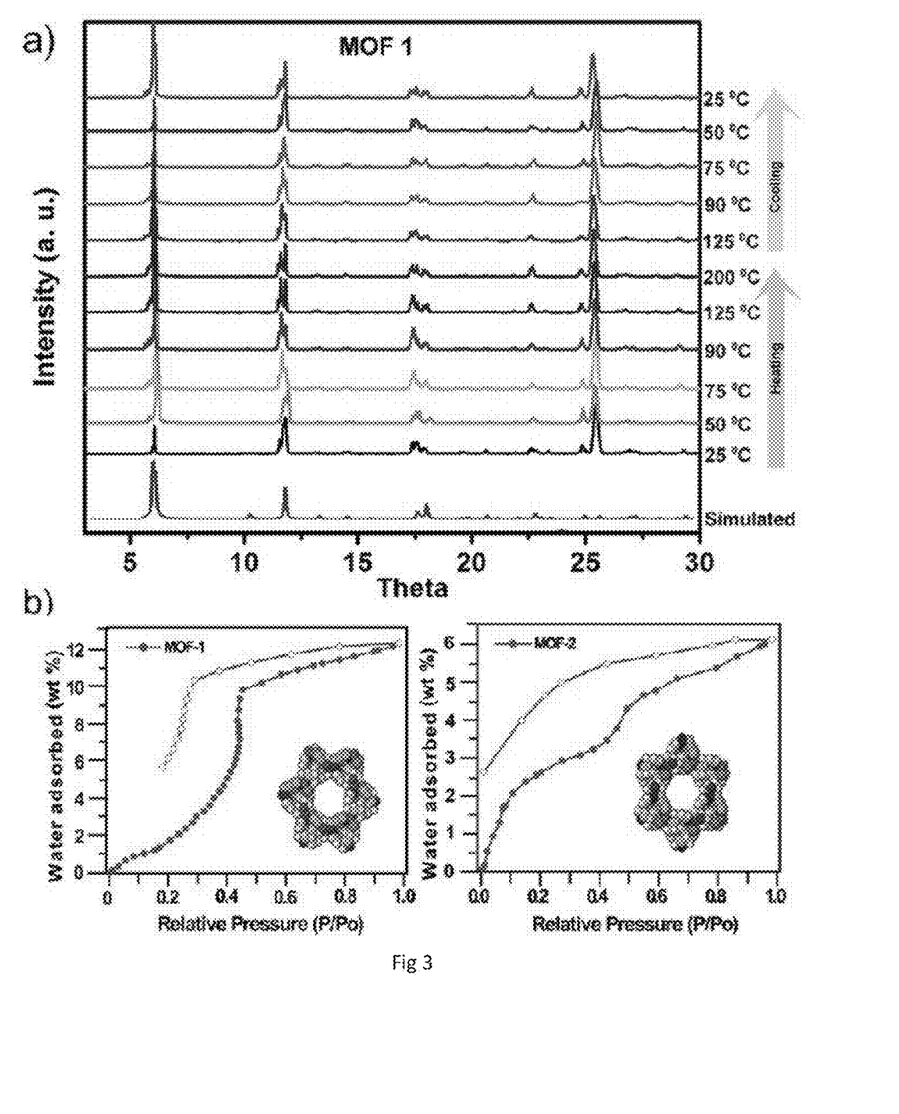
FIG. 3 represents (a) In situ variable-temperature powder X-ray diffraction (VT-PXRD) of MOF 3 upon both heating (25-200° C.) and cooling (200-25° C.). This VT-PXRD experiment shows that the framework is stable and remains crystalline over a wide range of temperatures and after solvent removal. (b) Water adsorption isotherm of MOF 1 and MOF 2 showing 12 and 6 wt % of adsorption, respectively, at relative pressure P/Po=0.9, wherein P actual pressure exerted by gas and Po=pressure exerted by gas at standard condition.

The phase purity of the bulk materials was confirmed by PXRD experiments, which are in good agreement with the simulated PXRD patterns. TGA performed on as-synthesized 1-4 MOFs revealed that these compounds have thermal stability up to ~270° C. The TGA trace for as synthesized 1, 2, 3 and 4 showed gradual weight-loss steps of ~7% (2H2O in 1 and 3, calcd 10.5%) and ~6% (2H2O in 2 and 4, calcd 9.3%) over a temperature range of 40-100° C., corresponding to escape of guest water molecules from the pores. We note that the water molecules of 1 and 2 were released without damaging the frameworks, as evidenced by the coincidence of the PXRD patterns of 1 and 2 samples heated to and held at 150° C. in a N2 atmosphere with the PXRD patterns simulated from single-crystal structures. The above fact is also verified by in situ VT-PXRD of MOF 1 and MOF 2. All major peaks of experimental and simulated PXRDs are well matched, indicating the sample's phase purity (FIG. 3a). A combined heating and cooling in situ VT-PXRD experiment reveals that the framework is stable, remains crystalline over a wide temperature range (heating from 25 to 200° C. and then cooling from 200 to 25° C.), and remains stable after solvent removal (solvent escape ~100° C., confirmed by TGA). Escape of water molecules from the crystals was also monitored by hot-stage microscopy at different temperature intervals (25-270° C.). Pictures taken on a hot-stage microscope reveal that the trapped water molecules escape the lattice between 60 and 120° C. as heating gees on and cracking appears on the crystal surface, but crystallinity remains intact up to 250° C. This observation indicates that it is possible to monitor the arrangement of water molecules with respect to temperature, and we can achieve a solvent-free framework after successful removal of solvent at higher temperatures.

It is noteworthy that the water molecules adopt similar arrangements in all MOFs 1-6 reported in this paper, except the handedness. The guest-free frameworks of MOFs 1-6 reported in this paper show high affinity for water, irrespective of different structural variation.

Figure 4:
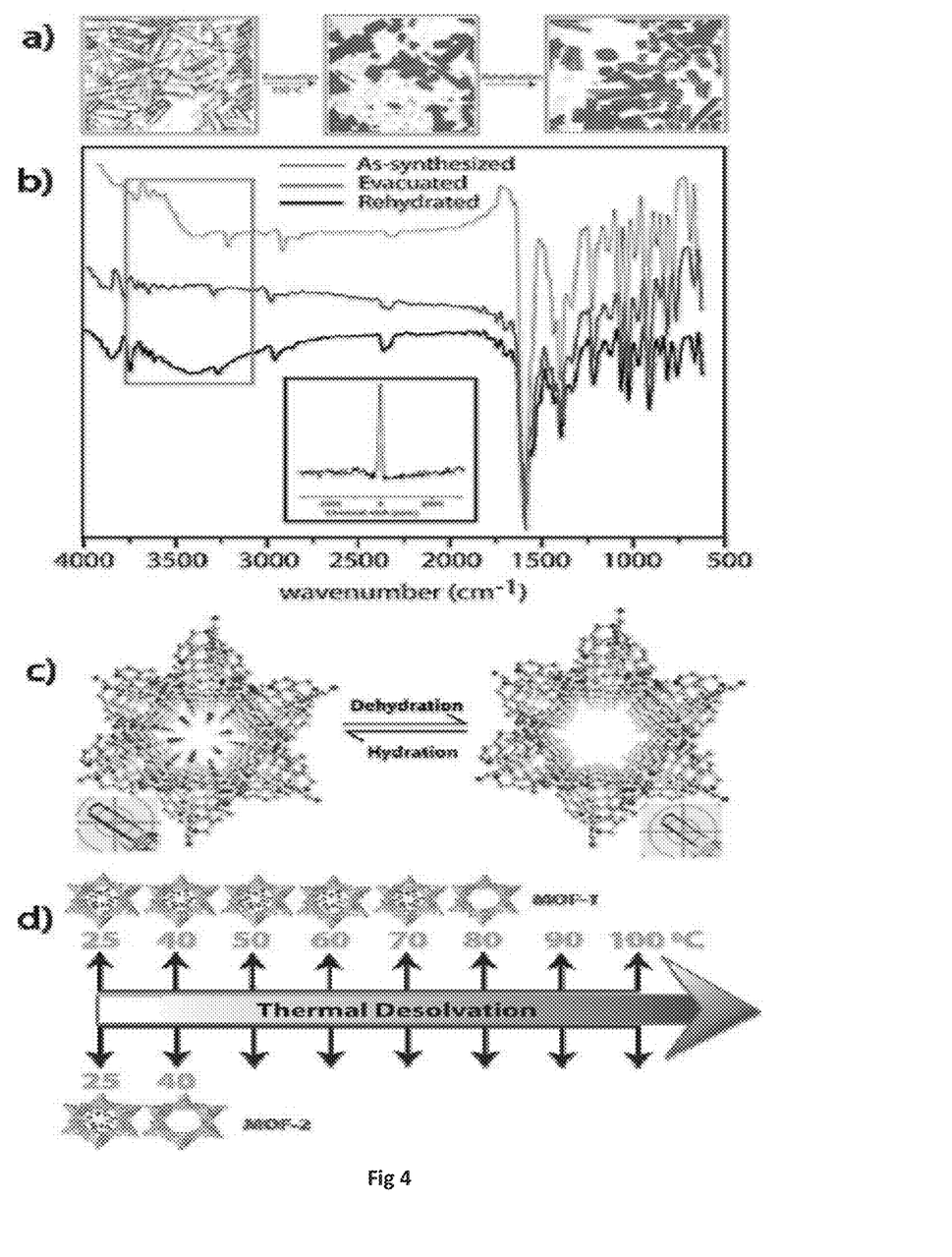

To provide further evidence of water affinity apart from crystallographic information, MOF 1 was extensively studied by various experiments. MOF 1 shows a reversible transformation in the presence of water vapor. After evacuation at 150° C. for 2 days, the dehydrated polycrystalline sample of 1 (confirmed by PXRD, IR, and TGA) was exposed in a closed chamber saturated with water vapor. The single-crystalline nature of MOF 1 comes back within 6-12 h (FIG. 4a), which is confirmed by IR, TGA, and crystallography. FT-IR spectra of the evacuated MOF 1 sample collected at time intervals of 1 h showed a gradual increase in the intensity of the water peaks after exposure of 1 to moisture (FIG. 4b), which further confirms the high affinity of 1 for water. The water affinity of 1 and 2 was also examined by water adsorption isotherms. Surprisingly, it was found that MOF 1 shows 12 wt % water vapor uptake (150 cm3/g at STP), whereas MOF2 shows 6 wt % (75 cm3/g at STP), about half at a relative pressure (P/Po) of 0.9 (FIG. 3b). It is quite clear that MOF 2 has less water affinity compared to MOF 1, though the framework arrangements in 1 and 2 are similar. The CO2 adsorption isotherm indicates much less uptake (25 cm3/g for 1 and 20 cm3/g for 2) than predicted on the basis of X-ray crystallography and indicates a low degree of interaction points inside the pore.

From TGA experiments, it was found that the MOFs lose lattice water molecules in the temperature range of 40-80° C. After careful observation of the collected data, it was found that 80° C. is the ideal temperature at which one could achieve a stable and solvent-free framework of 1 with reasonably good data [R1=6.4%, wR2=14.7%, GOF=1.005]; below that temperature, water stays in the lattice as solvent and the framework remains intact, but high thermal vibration observed in some of the atom sites results in high refinement parameters (FIG. 4d). A similar experiment performed on MOF 2 (Br analogue' of MOF 1) reveals that one can achieve an evacuated framework at a much lower temperature of 40° C. [R1=5.7%, wR2=15.12%. GOF=1.071]. So far, the amount of water uptake of MOF1 with respect to MOF 2 and the achievement of an evacuated framework of MOF 2 at only 40° C. clearly indicate that MOF 2 has a lower water affinity than MOF 1. It has been mentioned already that the structural arrangements of MOFs 1-6 are all similar, except for the handedness and halogen atoms in the framework [M-X, X=—Cl, —Br, —CH3COO, —HCOO)]. The X-ray crystal structures of 1-6 established that these materials are amenable to proton-conduction owing to the continuous (O . . . O) helical 1D water chain ($D_{O \ldots O}$=3.234(3)Å) in a confined hydrophobic and acidic environment ($D_{O \ldots Cl-M}$=3.164 Å, $D_{O \ldots Br-M}$=3.175 Å).

The invention provides the proton conductivity of the MOFs 1 to 4, The proton conductivities of two halogen isomers, 1 and 3, were measured by a quasi-two-probe method, with a Solartron 1287 electrochemical interface with frequency response analyzer. The conductivities were determined from the semicircles in the Nyquist plots (FIG. 5. The proton conductivities of 1 and 3 were $4.45 \times 10^{-5}$ and $4.42 \times$ $10^{-5}$ S cm$^{-1}$, respectively, at 304 K and 98% relative humidity (RH). This value, was highly humidity dependent and dropped to 1.49×10$^{-5}$ and 1.22×10$^{-5}$ S cm4 at 75% and 60% RH, respectively, at 304 K.

Surprisingly, 2 and 4 show almost zero proton conductivity after testing the proton conduction' 4-5 times on different batches of samples. The above anomalous behavior is attributed to a few reasons: (1) the water holding capacity of MOF 2 is less than that of MOF 1, confirmed by water adsorption; (2) at room temperature (~35° C.), MOF 1 has a continuous water chain, while MOF 2 has a discrete water assembly, confirmed by VT-SCXRD experiments; (3) the interior cavities with halogen atoms with different electro-negativities are hydrogen bonded to water molecules. The present results also supported the lower water adsorption property shown by MOF 2 (6 wt %) compared to MOF 1 (12 wt %), as discussed previously.

To prove the role of water molecules, we synthesized 1-D$_2$O [Zn(l-L$_{Cl}$)(Cl)(D$_2$O)], taking D$_2$O as solvent of synthesis. 1-D$_2$O was studied further by IR and 2H SSNMR, which confirmed the D$_2$O incorporation in 1-D$_2$O and its structural similarity to MOF 1.

Figure 5:
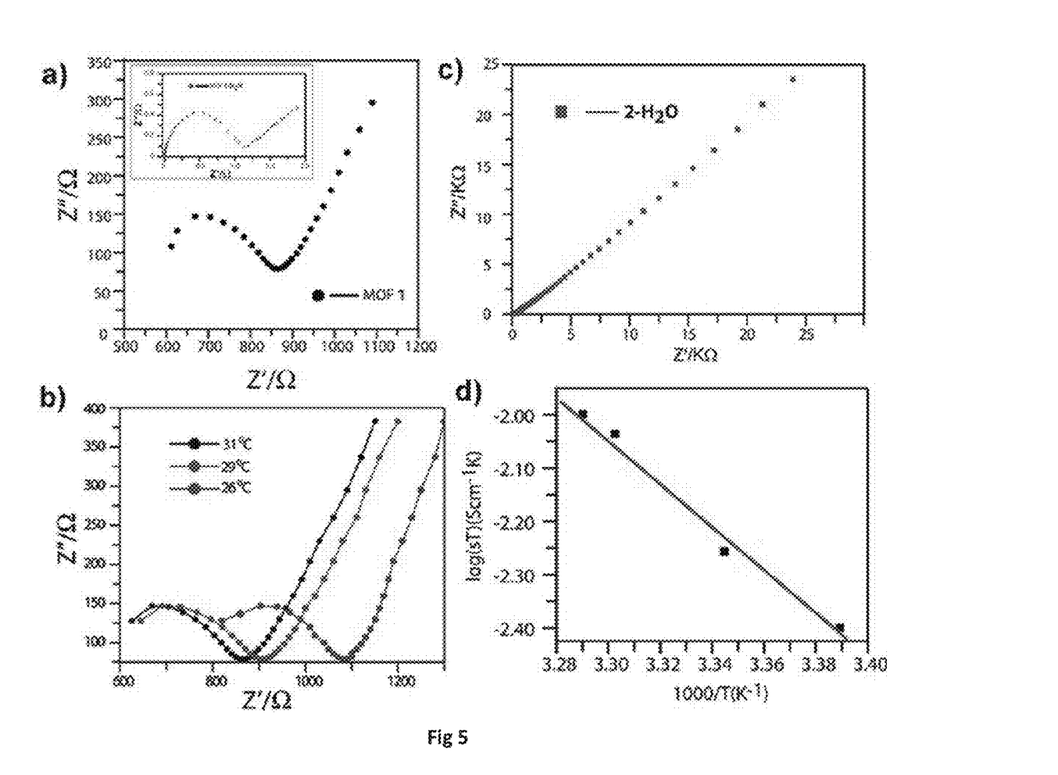
FIG. 5 represents (a) Proton conductivity data comparison of MOF 1 and 1-$D_2O$ (inset) at 98% relative humidity (RH) showing decreasing proton conductivity value after $D_2O$ substitution. (b) Temperature-dependent proton conductivity values of MOF 1 at different temperatures. (c) Proton conductivity of MOF 2 at 98% RH, showing zero proton conduction as compared to MOF 1 under similar conditions. (d) Arrhenius plots of proton conductivity of MOF 1.
Figure 6:
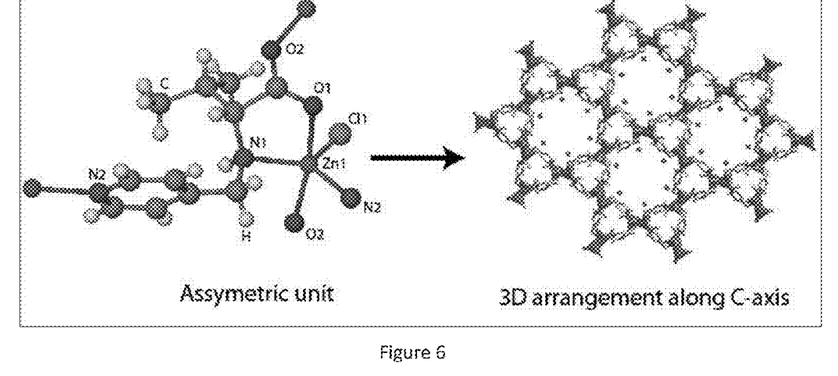
Figure 7:
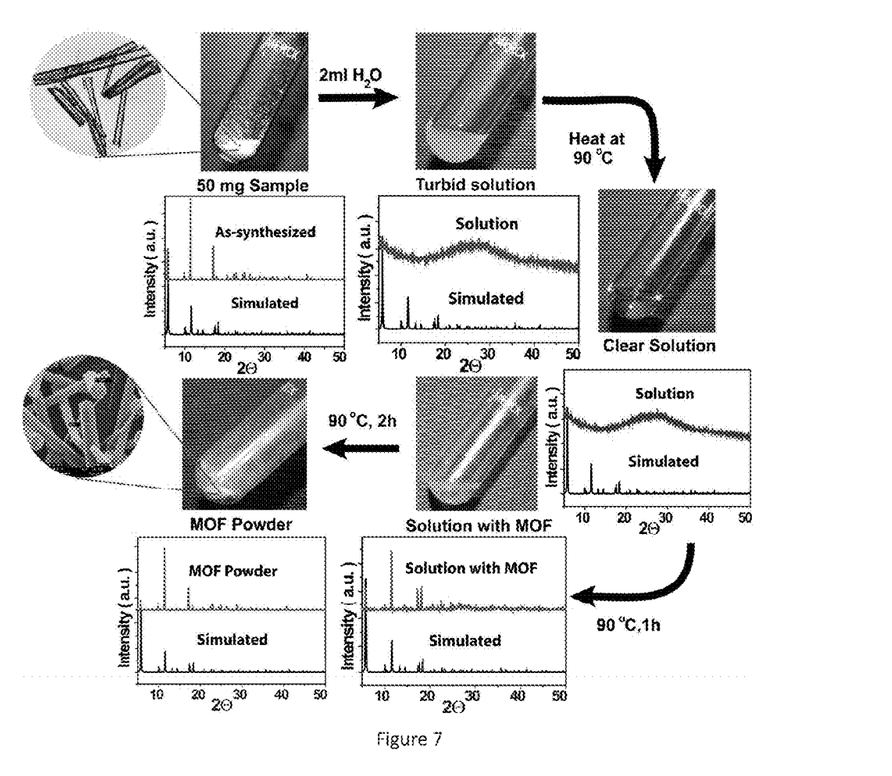

Impedance studies on the deuterated sample in a H2 atmosphere humidified (98%) with D$_2$O gave a conductivity value of 1.33×10$^{-5}$ S cm-1. The lower value is expected due to the heavier isotopic substitution. Proton conductivity measurements performed at different temperatures show a gradual increase in proton conductivity from 3.13×10$^{-5}$ to 4.45×10$^{-5}$ S cm$^{-1}$ as the temperature is increased from 299 to 304 K, respectively (FIG. 5b). At higher temperatures, above. 40° C., the proton conductivity of 1 decrease due to partial dehydration, as indicated by a TGA plot, and the 2H SSNMR data had indicated mobile protons/deuterons even at 25° C. The above result concludes the fact that MOFs having higher water holding capacity has the better proton conductivity over the MOFs having lower water holding capacity.

The ordered water molecules anchored by weak metal halogen groups facilitate proton conduction, as confirmed by proton conductivity measurements coupled with deuterium exchange and solid-state (SS) NMR experiments.

The activation energies (Ea) for the proton transfer derived from the bulk conductivity of 1 and 3 were 0.34 and 0.36 eV, respectively, as determined from least-squares fits of the slopes. MOF 1 show a higher Ea value than Nafion (0.22 eV), 25b but comparable with those of Zr(HPO4)2 (0.33)25c and HUO2PO4 3 4H2O (0.32 eV).25d This low Ea observed in 1 indicates that the ordered helical water chain (observed crystallographically) functions to transport protons via a Grotthuss hopping mechanism, as opposed to the higher Ea value, observed for a vehicular transfer mechanism. The proton conductivity value of MOF 1 is higher than those of MIL-53-based MOFs (~10$^{-6}$10$^{-9}$ S cm reported by Kitagawa et al. at 25° C., 95% RH) and comparable to that of a zinc-phosphonate MOF (1.33×10$^{-5}$ S cm$^{-1}$ reported by Shimizu et al. at 25° C., 98% RH) but lower than those of ferrous oxalate dihydrate (1.3×10$^{-3}$ S cm$^{-1}$ at 25° C., 98% RH) and cucurbit [6]uril (1.1×10$^{-3}$ S cm$^{-1}$ at 25° C., 98% RH) under similar conditions.

By judicial choice of different metal ions stated above and various derivative of amino acids shown above (where variation in the derivative of amino acids back bone can be easily made by changing both amino acid residue and aromatic groups), it will become obvious to one skilled in the art to synthesize a wide verity of different MOFs. Such synthesized MOFs and examples given are merely an illustration of the instant invention and should not be construed as limiting the scope of the present invention in any manner means that innumerous MOFs can be prepared using varying the R1, R2 and metal ion and only limited MOFs are presented here for examples.

EXAMPLES

Following examples are given by way of illustration therefore should not be construed to limit the scope of the invention.

Materials and General Methods

All reagents were commercially available and used as received. Powder X-ray diffraction patterns were recorded on a Phillips PANalytical diffractometer with Cu Kα irradiation (A=1.5406 Å), a scan speed of 2° min$^{-1}$, and a step size of 0.02° in 2θ. Fourier transform (FT)IR spectra (KBr pellet) were obtained on a Perkin Elmer FT-IR spectrometer (Nicolet). Thermogravimetric analysis was carried out in the temperature range of 25-800° C. on an SDT Q600 TG-DTA analyzer under aN2 atmosphere at a heating rate of 10° C. min-1. All low-pressure CO2 adsorption experiments (up to 1 bar) were performed on a Quantachrome Quadrasorb automatic volumetric instrument. All low-pressure water adsorption experiments (up to 1 bar) were performed on a BEL-SORPmax volumetric instrument. A Leica M-80 optical, microscope with hot stage and camera attachment was used for collecting photographs. Proton conductivity data were measured by a quasi-two-probe method, with a Solartron 1287 electrochemical interface and a frequency response analyzer; circular dichroism data were measured with a JASCO J-851-150 L CD spectropolarimeter. Solid-state NMR spectra were recorded with a Bruker 300 MHz NMR spectrometer, and ligand NMR spectra were recorded with a Bruker 200 MHz NMR spectrometer.

Comparative Examples 1 to 7

Example 1

N-(4-Pyridylmethyl)-L-valine.HCl [1-L$_{Cl}$]

The ligand N-(4-pyridylmethyl)-L-valine.HCl (1-L$_{Cl}$) was prepared using a modified literature procedure. To an aqueous solution (10 mL) of L-valine (2 g, 17 mmol) and Na$_2$CO$_3$ (0.91 g, 8.5 mmol), 4-pyridinecarboxaldehyde (1.82 g, 17 mmol) in MeOH (10 mL) was added slowly. The solution was stirred for 1 h and cooled in an ice bath. NaBH$_4$ (0.76 g, 20.4 mmol) in 10 ml of water was added. The mixture was stirred for 1 h, and 3 N HCl, was used to adjust the pH to 6. The solution was stirred further for 2 h and then evaporated to dryness. The solid was extracted in hot and dry MeOH (150 mL×3), and the filtrate was evaporated to get a white powder. Yield: 2.9 g, 70% yield. IR (KBr, cm$^{-1}$): vOH, 3421; vas (CO$_2$), 1562; vs(CO$_2$), 1409.

1H NMR (D$_2$O, ppm): —CH$_3$ (1.21, d, 3H), —CH$_3$ (1.35, d, 3H), —CH (3.20, m, 1H), —HN—CH (3.65, m, 1H), —CH2 (3.82, dd, 2H), py-H (7.34, d, 2H), py-H (8.38, d, 2H).

Example 2

N-(4-Pyridylmethyl)-L-valine.HBr [1-L$_{Br}$]

The ligand N-(4-pyridylmethyl)-L-valine.HBr (1-L$_{Br}$) was prepared exactly as 1-LCl, except HBr was used instead of HCl for off adjustment (i.e. 5.5). Yield: 3.4 g, 70%. IR (KBr, cm$^{-1}$): vOH, 3420; vas(CO$_2$), 1560; vs(CO$_2$), 1411.

1H NMR (D$_2$O, ppm): —CH$_3$ (1.20, d, 31-1), —CH$_3$ (1.33, d, 3H), —CH (3.24, m, 1H), —HN—CH (3.63, m, 1H), —CH$_2$ (3.79, dd, 2H), py-H (7.34, d, 2H), py-H (8.37, d, 2H).

Example 3

N-(4-Pyridylmethyl)-D-valine.HCl [d-L$_{Cl}$]

The ligand N-(4-pyridylmethyl)-D-valine. HCl (d-L$_{Cl}$) was prepared exactly as (l-L$_{Cl}$), except D-valine was used instead of L-valine. Yield: 3.1 g, 72%.

IR (KBr, cm$^{-1}$): vOH, 3417; vas(CO$_2$), 1564; vs(CO$_2$), 1415.

1H NMR (D$_2$O, ppm): —CH$_3$ (1.21, d, 3H), —CH$_3$ (1.34, d, 3H), —CH (3.22, m, 1H), —HN—CH (3.65, m, 1H), —CH$_2$ (3.78, dd, 2H), py-H (7.30, d, 2H), py-H (8.36, d, 2H).

Example 4

N-(4-Pyridylmethyl)-D-valine.HBr [d-L$_{Br}$]

The ligand N-(4-pyridylmethyl)-D-valine.HBr (d-L$_{Br}$) was prepared exactly as l-L$_{Br}$, except D-valine was used instead of L-valine. Yield, 3.6 g, 72%.

IR (KBr, cm$^{-1}$): vOH, 3419; vas(CO$_2$), 1570; vs(CO$_2$), 1421.

1H NMR (D$_2$O, ppm): —CH$_3$ (1.20, d, 3H), —CH$_3$ (1.34, d, 3H), —CH (3.24, m, 1H), —HN—CH (3.63, m, 1H), —CH$_2$ (3.80, dd, 2H), py-H (7.35, d, 2H), py-H (8.37, d, 2H).

Example 5

[Zn(l-L1$_{Cl}$)(Cl)](H$_2$O)$_2$ (1)

To an aqueous solution (2 mL) of l-L$_{Cl}$ (0.044 g, 0.2 mmol), Zn(CH3COO)2 0.2H2O (0.022 g, 0.1 mmol) was added and sonicated for 10 min. The clear solution was kept in a tightly capped 5 mL vial for 24 h at 90° C. to produce rod-shaped transparent crystals. Yield: 0.025 g, 71%.

IR (KBr, cm1): vOH, 3421; vNH, 2977; vas(CO2), 1589; vs(CO2), 1395; vCN, 1626.

Elemental analysis: calcd C (38.8%), H (4.44%), N (8.23%). Found C (38.78%), H (4.41%), N (8.25%).

Example 5

[Zn(l-L1$_{Br}$)(Br)](H2O)2 (2)

To an aqueous solution (2 mL) of l-L$_{Br}$ (0.044 g, 0.2 mmol), Zn(CH3COO)2.2H2O (0.022 g, 0.1 mmol) was added and sonicated for 10 min. The clear solution was kept in a tightly capped 5 mL vial for 24 h at 90° C. to produce rod-shaped transparent crystals. Yield: 0.026 g, 67%.

IR (KBr, cm1): vOH, 3427; vNH, 2974; vas(CO2), 1590; vs(CO2), 1394; vCN, 1623.

Elemental analysis: calcd C (34.37%), H (3.90%), N (7.29%). Found C (34.35%), H (3.92%), N (7.25% Y.

Example 6

[Zn(d-L1$_{Cl}$)(Cl)](H$_2$O)$_2$ (3)

To an aqueous solution (2 mL) of d-L$_a$ (0.044 g, 0.2 mmol), Zn(CH3COO)2. 2H2O (0.022 g, 0.1 mmol) was added and sonicated for 10 min. The clear solution was kept in a tightly capped 5 mL vial for 24 h at 90° C. to produce rod-shaped transparent crystals. Yield: 0.023 g, 71%.

IR (KBr, cm1): vOH, 3420; vNH, 2975; vas(CO2), 1589; vs(CO2), 1397; vCN, 1627.

Elemental analysis: calcd C (38.82%), H (4.44%), N (8.23%). Found C (38.79%), H (4.42%), N (8.24%).

Example 7

[Zn(d-L1Br)(Br)](H2O)2 (4)

To an aqueous solution (2 mL) of d-L$_B$, (0.044 g, 0.2 mmol), Zn(CH3COO)2. 2H2O (0322 g, 0.1 mmol) was added and sonicated for 10 min. The clear solution was kept in a tightly capped 5 mL vial for h at 90° C. to produce rod-shaped transparent crystals. Yield. 0.026 g, 69%.

| | | | |
|---|---|---|---|
| Empirical formula | C$_{11}$H$_{15}$ClN$_2$O$_3$Zn | Formula weight | 324.09 |
| CCDC No. | 831054 | Wavelength | 0.71073 Å |
| Temperature | 296(2) K | Volume | 2862.76(6) Å$^3$ |
| Crystal system | Hexagonal | Z | 6 |
| Space group | P6$_1$ | Density (calculated) | 1.128 |
| Unit cell dimensions | a = 17.691(2) Å | Absorption coefficient | 1.427 |
| | b = 17.691(2) Å | | |
| | c = 10.5617(12) Å | | |
| | γ = 120 | | |
| F(000) | 996 | Reflections collected | 4581 |
| Independent reflections | 4302 | Goodness-of-fit on F2 | 1.065 |
| Final R indices [I > 2sigma(I)] | R1 = 0.0408, wR2 = 0.1423 | R indices (all data) | R1 = 0.0456, wR2 = 0.1467 |

| Atoms | Bond lengths (Å) | | Bond Angles (°) |
|---|---|---|---|
| Zn1N1 | 2.090(2) | Zn1Cl/Br | 2.2389(14) |
| Zn1N2 | 2.057(3) | N2Zn1N1 | 116.48(13) |
| Zn1O1 | 2.167(3) | N2Zn1O2 | 89.83(12) |
| Zn1O2 | 2.093(3) | N1Zn1O2 | 91.61(11) |
| | | N2Zn1O1 | 91.71(11) |
| | | N1Zn1O1 | 78.60(9) |
| | | O2Zn1O1 | 169.71(11) |
| | | N2Zn1Cl/Br | 115.45(10) |
| | | N1Zn1Cl/Br | 127.87(9) |
| | | O2Zn1Cl/Br | 92.77(10) |
| | | O1Zn1Cl/Br | 95.75(8) |

IR (KBr, cm1): vOH; 3425; vNH, 2970; vas(CO2), 1592: vs(CO2), 1395; vCN, 1622.

Elemental analysis: calcd C (34.37%), H (3.90%), N (7.29%). Found C (34.36%), H (3.91%), N (7.27%).

Examples 8 to 20

Example 8

(4-Pyridylmethyl)-L-valine.CH$_3$COOH [l-L$_{CH3COO}$]

The ligand N-(4-pyridylmethyl)-L-valine.CH$_3$COOH (l-L$_{CH3COO}$) was prepared exactly as l-L$_{Cl}$, except CH$_3$COOH was used instead of HCl for pH adjustment. Yield: 3.6 g, 70%.

IR (KBr, cm1): vOH, 3420; vas(CO2), 1560; vs(CO2), 1411.

1H. NMR (D$_2$O, ppm): —CH$_3$ (1.20, d, 3H), —CH$_3$ (1.33, d, 3H), —CH (3.24, m, 1H), —HN—CH (3.63, m, 1H), —CH$_2$ (3.79, dd, 2H), py-H (7.34, d, 2H), py-H (8.37, d, 2H).

Example 9

N-(4-Pyridylmethyl)-L-valine.HCOOH[l-L$_{HCOO}$]

The ligand N-(4-pyridylmethyl)-L-valine.HCOOH (l-L$_{HCOO}$) was prepared exactly as l-L$_{Cl}$, except HCOOH was used instead of HCl for pH adjustment. Yield: 3.5 g, 70%. IR (KBr, cm1): vOH, 3420; vas(CO2), 1560; vs(CO2), 1411.

1H NMR (D$_2$O, ppm): —CH$_3$ (1.20, d, 3H), —CH$_3$ (1.33, d, 3H), —CH (3.24, m, 1H), —HN—CH (3.63, m, 1H), —CH2 (3.79, dd, 2H), py-H (7.34, d, 2H), py-H (8.37, d, 2H).

Example 10

N-(4-pyridylmethyl)-L-alanine.HCl (l-L1$_{Cl}$)

The ligand N-(4-pyridylmethyl)-L-alanine. HCl (l-L1$_{Cl}$) was prepared using a modified literature procedure. To an aqueous solution (10 mL) of L-alanine (1.78 g, 17 mmol) and Na$_2$CO$_3$ (0.91 g, 8.5 mmol), 4-pyridinecarboxaldehyde (1.82 g, 17 mmol) in MeOH (10 mL) was added slowly. The solution was stirred for 1 h and cooled in an ice bath. NaBH$_4$ (0.76 g, 20.4 mmol')' in 10 mL of water was added. The mixture was stirred for 1 h, and 1 N Ha was used to adjust the pH to 6-7. The solution was stirred further for 2 h and then evaporated to dryness. The solid was extracted in hot and dry MeOH (150 mL×3), and the filtrate was evaporated to get a white powder. Yield: 2.7 g, 75% yield.

Example 11

N-(4-Pyridylmethyl)-L-alanine.HBr [l-L1$_{Br}$]

The ligand N-(4-pyridylmethyl)-L-alanine. HBr (l-L1$_{Br}$) was prepared using same procedure as described for Example 11, only HBr was used instead of HCl for pH adjustment of 5.5-6. Yield: 2.9 g, 72% yield.

Example 12

N-(4-Pyridylmethyl)-L-alanine.CH$_3$COOH [l-L1$_{CH3COO}$]

The ligand N-(4-pyridylmethyl)-L-alanine. CH$_3$COOH (l-L1$_{CH3COO}$) was prepared using same procedure as described for Example 11, only CH$_3$COOH was used instead of HCl for pH adjustment of 6.2-6.5: Yield: 2.9 g, 70% yield.

Example 13

N-(4-Pyridylmethyl)-L-alanine.HCOOH[l-L1$_{HCOO}$]

The ligand N-(4-pyridylmethyl)-L-alanine.HCOOH(l-L1$_{HCOO}$) was prepared using same procedure as described for Example 11, only HCOOH was used instead of HCl for pH adjustment of 5.7-6. Yield: 2.7 g, 72% yield.

Example 14

[Zn(l-L1$_{CH3COO}$)(CH3COO)](H2O)2 (5)

To an aqueous solution (0.5 ml) of l-L$_{CH3COO}$ (0.046 g, 0.2 mmol) Zn(CH$_3$COO)$_2$.2H$_2$O (0.022 g, 0.1 mmol) in 5 ml MeOH was added and sonicated for 10 min. The clear solution was kept in a 15 mL vial for 24 h to produce rod-shaped transparent crystals. Yield: 0,028 g, 71%.

Example 15

[Zn(l-L1$_{HCOO}$)(HCOO)](H2O)2 (6)

To an aqueous solution (0.5 mL) of l-L$_{HCOO}$ (0.046 g, 0.19 mmol), Zn(CH$_3$COO)$_2$.2H$_2$O (0.022 g, mmol) in 5 ml MeOH was added and sonicated for 10 min. The clear solution was kept in a 15 mL vial for 24 h to produce rod-shaped transparent crystals. Yield: 0.027 g, 71%.

Example 16

[Zn(l-L2$_{Cl}$)(Cl)](H2O)2 (7)

To an aqueous solution (0.25 mL) of l-L1$_{Cl}$ (0.045 g, 0.19 mmol), Zn(CH$_3$COO)$_2$.2H$_2$O (0.020 g, 0.09 mmol) in 5 ml MeOH was added and sonicated for 10 min. The clear solution was kept in a 15 mL vial for 24 h to produce rod-shaped transparent crystals. Yield: 0.026 g, 70%.

| Empirical formula | C9H11ClN2O4Zn | Formula weight | 312.04 |
|---|---|---|---|
| Radiation type | Mo/K$_\alpha$ | Wavelength | 0.71073 Å |
| Temperature | 293(2) K what is 2 in this value. | Volume | 2777.4(5) Å$^3$ |
| Crystal system | Hexagonal | Z | 6 |
| Space group | P6$_1$ | Density (calculated) | 1.119 |
| Unit cell dimensions | a = 17.6588(13) Å | Absorption coefficient | 1.473 |
| | b = 17.6588(13) Å | | |
| | c = 10.2847(6) Å | | |
| | γ = 120 | | |
| F(000) | 948 | Reflections collected | 3431 |

-continued

| | | | |
|---|---|---|---|
| Independent reflections | 2889 | Goodness-of-fit on F2 | 1.119 |
| Final R indices [I > 2sigma(I)] | R1 = 0.0665, wR2 = 0.1946 | R indices (all data) | R1 = 0.0818, wR2 = 0.2301 |

| Atoms | Bond lengths (Å) | | Bond Angles (°) |
|---|---|---|---|
| Zn1N1 | 2.081(6) | Zn1Cl/Br | 2.220(4) |
| Zn1N2 | 2.044(7) | N2Zn1N1 | 122.5(3) |
| Zn1O1 | 2.190(6) | N2Zn1O2 | 88.0(3) |
| Zn1O2 | 2.124(7) | N1Zn1O2 | 88.9(3) |
| | | N2Zn1O1 | 90.7(3) |
| | | N1Zn1O1 | 76.4(2) |
| | | O2Zn1O1 | 161.6(3) |
| | | N2Zn1Cl/Br | 113.0(3) |
| | | N1Zn1Cl/Br | 124.2(3) |
| | | O2Zn1Cl/Br | 98.8(3) |
| | | O1Zn1Cl/Br | 98.6(2) |

Example 17

[Zn(l-L2$_{Br}$)(Br)](H2O)2 (8)

To an aqueous solution (0.4 mL) of l-L1$_{Br}$ (0.048 g, 0.19 mmol), Zn(CH$_3$COO)$_2$.2H$_2$O (0.021 g, 0.95 mmol) in 5 ml MeOH was added and sonicated for 10 min. The clear solution was kept in a 15 mL vial for 12 h, to produce rod-shaped transparent crystals. Yield: 0.029 g, 70%.

Example 18

[Zn(l-L2$_{CH3COO}$)(CH3COO)](H2O)2 (9)

To an aqueous solution (0.2 mL) of l-L1$_{CH3COO}$ (0.046 g, 0.2 mmol), Zn(CH$_3$COO)$_2$.2H$_2$O (0.020 g, 0.9 mmol) in 8 ml MeOH was added and sonicated for 10 min. The clear solution was kept in a 15 mL vial for 36 h to produce rod-shaped transparent crystals. Yield: 0.025 g, 65%.

Example 19

[Zn(l-L2$_{HCOO}$)(HCOO)](H2O)2 (10)

To an aqueous solution (0.1 mL) of l-L1$_{HCOO}$ (0.045 g, 0.2 mmol), Zn(HCOO)$_2$.2H$_2$O (0.022 g, 0.1 mmol) in 10 ml MeOH was added and sonicated for 10 min. The clear solution was kept in a 15 mL vial for 24 h to produce rod-shaped transparent crystals. Yield: 0.025 g, 75%.

Example 20

Water Solubility of MOF 50 mg of MOF as prepared in example 2 was dissolved in 10 ml of water by boiling it for 5 minutes to get a clear solution. After allowing, water to evaporate overnight, the crystallized MOF was tested again and found to match the coordinates of the MOF of examples 1 and 2.

| MOF | Solubility |
|---|---|
| MOF 1 | 22 mg/ml |
| MOF 2 | 20 mg/ml |
| MOF 3 | 22 mg/ml |
| MOF 4 | 20 mg/ml |
| MOF 5 | 25 mg/ml |
| MOF 6 | 26 mg/ml |

-continued

| MOF | Solubility |
|---|---|
| MOF 7 | 25 mg/ml |
| MOF 8 | 21 mg/ml |
| MOF 9 | 27 mg/ml |
| MOF 10 | 28 mg/ml |

Example 21

Proton Conductivity of MOFs

| MOFs | PROTON CONDUCTIVITY |
|---|---|
| MOF 1 | 4.45 × 10$^{-5}$ S cm$^{-1}$ |
| MOF 2 | NO PROTON CONDUCTIVITY |
| MOF 3 | 4.42 × 10$^{-5}$ S cm$^{-1}$ |
| MOF 4 | NO PROTON CONDUCTIVITY |
| MOF 5 | NO PROTON CONDUCTIVITY |
| MOF 6 | 3.6 × 10$^{-5}$ S cm$^{-1}$ |
| MOF 7 | 3.5 × 10$^{-3}$ S cm$^{-1}$ |
| MOF 8 | NO PROTON CONDUCTIVITY |
| MOF 9 | NO PROTON CONDUCTIVITY |
| MOF 10 | 2.2 × 10$^{-4}$ S cm$^{-1}$ |

ADVANTAGES OF THE INVENTION

This easy one step solution-state processing of proton conducting homochiral MOF will provide us an environment friendly low cost pathway for casting MOF films and many other things for industrial applications. Further control over MOF solubility and proton conductivity has been demonstrated by suitable choice of ligand and anion, which will be another advantageous effort for tailor made materials for different applications.

We claim:
1. Metal organic frameworks (MOFs) of Formula I

[M(l/d-L$_x$)(X)](H$_2$O)$_2$     Formula I wherein

M is a metal selected from the group consisting of Sc, Ti, V, Cr, Mn, Fe, Co, Ni, Cu, Zn, Y, Zr, Nb, Mo, Tc, Ru, Rh, Pd, Cd, La, W, Os, Ir, Pt, Au, Hg, Sm, Eu, Gd, Tb, Dy, Ho, Al, Ga, In, Ge, Sn, Pb), Li, Na, K, Rb, Cs, Mg, Ca, Sr or Ba;

L is derivatives of an amino acid ligand of Formula II

Formula II wherein $R_1$ is methyl or isopropyl; $R_2$ is selected from the group consisting of pyridyl, bipyridyl, imidazolyl, pyrimidinyl, 4-(pyridin-4-yl)phenyl, napthalyl, quinolinyl, and tetrazolyl;

X is $CH_3COO$ or $HCOO$ when $R_1$ is isopropyl; and

X is Cl, Br, $CH_3COO$ or $HCOO$ when $R_1$ is methyl.

2. The metal organic frameworks according to claim 1, wherein the metal organic frameworks are selected from the group consisting of:

[Zn(l-L1$_{CH3COO}$)($CH_3COO$)]($H_2O$)$_2$ (5); wherein $R_1$ is isopropyl, and $R_2$ is pyridyl;

[Zn(l-L1$_{HCOO}$)($HCOO$)]($H_2O$)$_2$ (6); wherein $R_1$ is isopropyl, and $R_2$ is pyridyl;

[Zn(l-L2$_{cl}$)(Cl)]($H_2O$)$_2$ (7); wherein $R_1$ is methyl, and $R_2$ is pyridyl;

[Zn(l-L2$_{Br}$)(Br)]($H_2O$)$_2$ (8); wherein $R_1$ is methyl, and $R_2$ is pyridyl;

[Zn(l-L2$_{CH3COO}$)($CH_3COO$)]($H_2O$)$_2$ (9); wherein $R_1$ is methyl, and $R_2$ is pyridyl; and

[Zn(l-L2$_{HCOO}$)($HCOO$)]($H_2O$)$_2$ (10); wherein $R_1$ is methyl, and $R_2$ is pyridyl.

3. The metal organic frameworks according to claim 1, wherein the derivative of an amino acid ligands of Formula II is selected from the group consisting of:

4. The metal organic frameworks as claimed in claim 1, wherein the water solubility of the compound of Formula I Formula II wherein $R_1$ is methyl or isopropyl; $R_2$ is selected from the group consisting of pyridyl, bipyridyl, imidazolyl, pyrimidinyl, 4-(pyridin-4-yl)phenyl, napthalyl, quinolinyl, and tetrazolyl; X=Cl, Br, $CH_3COO$ or $HCOO$ when methyl or isopropyl is in the range of 20-28 mg/ml.

5. The metal organic frameworks according to claim 1, wherein the metal organic frameworks are useful for proton conduction.

6. The metal organic frameworks according to claim 1, wherein the proton conductivity of the metal organic frameworks is in the range of $3.6 \times 10^{-5}$ S cm$^{-1}$ to $3.5 \times 10^{-3}$ S cm$^{-1}$.

7. A process for the preparation of the metal organic frameworks of claim 1, comprising the steps of:

a) adding a metal salt to an aqueous solution of a derivative of an amino acid ligand of Formula II in a suitable container in a ratio of metal salt to derivative of an amino acid ligand of Formula II ranging between 1:1 to 1:2 followed by sonicating to obtain a solution;

b) capping the container; and c) keeping the capped container as obtained in step (a) undisturbed at temperature in the range of 50 to 90° C. to obtain crystals of metal organic framework of Formula I.

8. The process according to claim 7, wherein the metal salt is zinc acetate.

9. Metal organic frameworks of Formula I

[M($l/d$-L$_x$)(X)]($H_2O$)$_2$    Formula I wherein

M is a metal selected from the group consisting of Sc, Ti, V, Cr, Mn, Fe, Co, Ni, Cu, Zn, Y, Zr, Nb, Mo, Tc, Ru, Rh, Pd, Cd, La, W, Os, Ir, Pt, Au, Hg, Sm, Eu, Gd, Tb, Dy, Ho, Al, Ga, In, Ge, Sn, Pb), Li, Na, K, Rb, Cs, Mg, Ca, Sr or Ba;

L is selected from the group consisting of wherein $R_1$ is methyl or isopropyl;
X is $CH_3COO$ or $HCOO$ when $R_1$ is isopropyl; and
X is Cl, Br, $CH_3COO$ or $HCOO$ when $R_1$ is methyl.

10. The metal organic frameworks of claim 1, wherein the metal organic frameworks are stable, water soluble, and biocompatible.

* * * * *